(12) United States Patent
van den Berg et al.

(10) Patent No.: US 10,850,004 B2
(45) Date of Patent: Dec. 1, 2020

(54) NERVE CAP AND PRODUCTION THEREOF

(71) Applicant: Polyganics IP B.V., Groningen (NL)

(72) Inventors: Pieter van den Berg, Groningen (NL); Hans Wicher Kuijper, Groningen (NL); Leendert Willem Schwab, Groningen (NL); Mariëtta Johanna Olga Elizabeth Bertleff, Groningen (NL); Harmen Hendrikus de Vries, Groningen (NL)

(73) Assignee: Polyganics IP B.V., Groningen (NL)

( * ) Notice: Subject to any disclaimer, the term of this patent is extended or adjusted under 35 U.S.C. 154(b) by 55 days.

(21) Appl. No.: 15/555,245

(22) PCT Filed: Mar. 7, 2016

(86) PCT No.: PCT/NL2016/050156
§ 371 (c)(1),
(2) Date: Sep. 1, 2017

(87) PCT Pub. No.: WO2016/144166
PCT Pub. Date: Sep. 15, 2016

(65) Prior Publication Data
US 2018/0339083 A1    Nov. 29, 2018

(30) Foreign Application Priority Data
Mar. 6, 2015 (NL) ..................... 2014410

(51) Int. Cl.
*A61B 90/00* (2016.01)
*A61L 27/18* (2006.01)
*A61L 27/58* (2006.01)
*A61L 27/38* (2006.01)

(52) U.S. Cl.
CPC .............. *A61L 27/18* (2013.01); *A61B 90/08* (2016.02); *A61L 27/3878* (2013.01); *A61L 27/58* (2013.01); *A61B 2090/0815* (2016.02)

(58) Field of Classification Search
CPC ....... A61L 27/18; A61L 27/3878; A61L 27/58; A61B 90/08
See application file for complete search history.

(56) References Cited

U.S. PATENT DOCUMENTS

| 4,198,842 A | 4/1980 | Pawlaczyk |
| 4,778,467 A | 10/1988 | Stensaas et al. |
| 2003/0147934 A1* | 8/2003 | Hissink et al. |
| 2013/0304174 A1 | 11/2013 | Langhals et al. |
| 2014/0094932 A1* | 4/2014 | Deister et al. |

FOREIGN PATENT DOCUMENTS

| CN | 1701083 A | 11/2005 |
| JP | 2005517062 A | 6/2005 |
| WO | 03/066705 A1 | 8/2003 |
| WO | 2014/130419 A1 | 8/2014 |

OTHER PUBLICATIONS

Dunnen, et al., "Poly(DL-lactide-epsilon-caprolactone) nerve guides perform better than autologous nerve grafts," Microsurgery. 1996;17(7):348-57.
Taneerananon, et al.,"Use of poly DL-lactide-e-caprolactone (Neurolac) conduit for enveloping traumatic neuromas," European Journal of Plastic Surgery vol. 36, pp. 657-660(2013).
Yan, et al.,"Mechanisms of Nerve Capping Technique in Prevention of Painful Neuroma Formation," PLoS ONE 9(4): e93973. https://doi.org/10.1371/journal.pone.0093973.

* cited by examiner

*Primary Examiner* — Alma Pipic
(74) *Attorney, Agent, or Firm* — Banner & Witcoff, Ltd.

(57) ABSTRACT

The invention is directed to a nerve cap for covering a nerve stump, comprising a tubular body with a closed end and an open end and essentially consisting of biodegradable polymeric material to prevent or treat symptoms caused by neuroma. The polymeric material preferably comprises a poly(DL-lactide-co-ε-caprolactone) copolymer obtained by the copolymerizaton of DL-lactide and ε-caprolactone, which copolymer has a lactide content of 51-75 mol %.

13 Claims, 2 Drawing Sheets

NERVE CAP AND PRODUCTION THEREOF

RELATED APPLICATION DATA

This application is a National Stage Application under 35 U.S.C. 371 of co-pending PCT application number PCT/NL2016/050156 designating the United States and filed Mar. 7, 2016; which claims the benefit of NL application number 2014410 and filed Mar. 6, 2015 each of which are hereby incorporated by reference in their entireties.

The invention relates to the field of nerve caps to treat and/or prevent symptoms caused by neuroma. In particular, the invention relates to nerve caps to cover neuroma at nerve stumps.

Neuroma is undesired growth of nerve tissue and typically occurs after nerve surgery or amputation of body parts. Neuroma typically develops in case of nerve damage. For instance, when a nerve is recovering from an injury, neuroma may form on the site of injury, i.e. between the proximal and distal ends of the nerves. Other scenarios, such as amputation of limbs or other parts of the body, may lead to an end neuroma. In such a case, part of the nerve is amputated resulting in a stump nerve from which an unorganized bulbous or nodular mass of nerve fibers may grow.

In particular cases a neuroma is a symptomatic neuroma that usually results in intermediate to severe pain and/or (extreme) discomfort such as itching to the patient. This possibly results in the inability of the patient to function (e.g. sleep or work) normally. A symptomatic neuroma may therefore have a large impact on a patient's life and it is therefore desirable to treat and/or prevent symptoms caused by neuroma.

To reduce or prevent symptoms resulting from end neuroma, a large variety of methods are known. These methods can roughly be divided into two categories: shortening or isolation of the nerve stump. A drawback of shortening the nerve stump is that neuroma may reoccur at the newly created transection of the nerve. The nerve stump may alternatively be isolated or covered by biological or synthetic materials to prevent the development of neuroma, thereby treating or preventing the concomitant symptoms. Galeano et al. describe in Microsurgery (2009)29 pages 568-572, the covering of a nerve stump by a cap of a vein to prevent formation of neuroma. Isolation of the nerve stump in a bone or muscle is also a method that is sometimes applied. In methods of isolation or covering of the nerve stump, if any (symptomatic) neuroma has already grown prior to the treatment, this neuroma is often first removed before the nerve stump is covered or isolated.

A synthetic cap, e.g. a silicone cap, is for instance described by Swanson et al. in the Journal of Hand Surgery (1977) pages 70-78.

US-A-2014/0094932 also describes a cap to cover the stump nerve. It is mentioned that both natural of synthetic biomaterials, such as high density polyethylene, polyethylene glycol hydrogen, purified proteins and decellularized tissue constructs can be used.

A drawback of biological materials is that the properties thereof, such a flexibility, absorption, degradation rate and the like, may not be sufficiently customizable. For instance, the properties of a vein are constant and may hardly be altered. The synthetic materials may have desirable customizability, but the materials used for the caps that are known do not have the desired properties. In particular, these synthetic materials are not biodegradable such that surgical removal is required or they remain the patient's body. This undesirably exposes the nerve to the risk of being damaged again. Alternatively, if the cap remains in the patients body the risk of further discomfort and complications such as infection or immune response increases.

Yan et al. describe in PLOS ONE 9(2014) pages e93973-e93973 the prevention of neuroma formation by capping the nerve stump with a cap in the shape of a tube having two open ends. A drawback of having two open ends is that the nerve may grow through the tube and from neuroma when it has passed the open end. To prevent this, surgeons may close the end that otherwise would remain open by suture. However, besides the fact that this method is impractical, there remains a large risk that the open end is not entirely closed and nerve may still grow through the tube.

A similar drawback is found in the method of Taneerananon et al. as described in European Journal of Plastic Surgery 2013(36) pages 657-660. Herein Taneerananon et al. described the use of a nerve conduit made of biodegradable material (poly DL-lactide-ε-caprolactone) for enveloping traumatic neuromas. It is shown that this treatment effectively works for neuromas that are formed between the proximal and distal ends of the injured nerve. However, since the nerve conduit has two open ends, it is less suitable for the prevention and/or treatment of pain and other symptoms caused by symptomatic neuroma by capping the nerve stumps.

It is therefore desirable to have a nerve cap for covering the nerve stump that solves at least one of the above-mentioned drawbacks and is e.g. customizable (i.e. synthetic), biodegradable and closed at one end.

The present inventors have found a nerve cap for covering a nerve stump, comprising a tubular body with a closed end and an open end and essentially consisting of biodegradable polymeric material. The nerve cap essentially consisting of biodegradable polymeric material means that the nerve cap consists of at least 90%, preferably at least 95%, most preferably at least 99% biodegradable polymeric material. It was found that the polymeric material described in WO 03/066705 (which is incorporated herein by its entirety) is particularly suitable for the present invention.

Hence, in a preferred embodiment of the present invention, the biodegradable polymeric material comprises a poly(DL-lactide-co-ε-caprolactone) copolymer obtained by the copolymerizaton of DL-lactide and ε-caprolactone, which copolymer has a lactide content of 51-75 mol %, preferably of 55-70 mol %, most preferably of 62-69 mol %.

The materials of the invention show excellent mechanical properties including stress-strain behavior, modulus and tensile strength, and excellent swelling behavior. Furthermore, the materials of the invention are completely amorphous. These properties make the materials of the invention very suitable for use as a nerve cap where both flexibility and mechanical strength are important characteristics.

The lactide (cyclic ester of two lactic acid molecules) is present in the copolymer as two lactic acid units.

The materials of the present invention combine flexibility with mechanical strength up to several weeks or months after implantation. Flexibility for example, is an important pre-requisite for handling and shaping, whereas mechanical strength is important from a protective point of view. Scaffolds, for example, should provide sufficient mechanical support to allow tissue regeneration and maturation.

According to the present invention the lactide content in the copolymer is at least 51 mol %. Although copolymers with lactide contents below 51% are highly flexible, these materials have a modulus and glass transition temperature (Tg) that is too low to give the devices composed thereof sufficient mechanical strength. Moreover, the extent of swelling of these materials is too high for nerve capping.

Copolymers with a lactide content higher than 75% exhibit generally insufficient flexibility to be applied for the intended medical applications. In particular, nerve caps composed of copolymers with lactide contents higher than 75% cannot be sutured easily to the nerve stumps using an 8-0, 9-0 or 10 0 stitch, because of too high rigidity.

Therefore, the copolymers of the present invention have a lactide content of 51 to 75 mol %, preferably from 55-70 mol % and most preferably from 62-69 mol %. For example, nerve caps of 65:35 (85/15 L/D)lactide-ε-caprolactone have better mechanical properties (modulus and tensile strength) than nerve caps produced using the same monomers, but in a 50:50 monomer ratio (e.g. initial tensile strength of 40-50 MPa vs 2.5 MPa).

The known copolymers (with a low lactide content) were found to have a relatively low glass transition temperature (−12° C. vs 14° C. of the polymers according to the present invention). This low glass transition temperature affects the mechanical properties (easier compression) and swelling properties. Furthermore, polymerization conditions affect the polymer properties, as will be shown later.

Nerve caps with the indicated preferred lactide contents will retain better mechanical properties during the covering of the nerve stump. The degree of swelling of these nerve caps can be very low, which prevents the risk of compression of the nerve stump. Moreover, the flexibility of these polymers is favorable with respect to interaction with and response of the surrounding tissue The mechanical properties and the degradation behavior, in particular swelling, of the copolymer of the present invention may further be adjusted by choosing the ratio of the L-enantiomer to D-enantiomer of the lactide in the copolymer (L/D-ratio). Preferred copolymers, having excellent mechanical properties (particularly swelling behavior), are those having a lactide L/D-ratio (mol/mol) of 65/35 to 95/5, preferably 70/30 to 90/10, most preferably about 85/15. The swelling behavior of these preferred copolymers makes them particularly suitable for use as nerve cap. Copolymers having a L/D ratio of more than 95/5 may give rise to formation of crystalline material.

Conversely, a copolymer having a lactide ratio of the D-enantiomer to L-enantiomer of the lactide (D/L-ratio) in the above-mentioned preferred ranges may be used with similar advantage. For practical reasons, however, it is preferred to prepare the polymers having the indicated L/D-ratios rather than the D/L-ratios, since the L-enantiomer is less expensive.

The biodegradable polymeric material according to the present invention may be produced by a conventional copolymerization reaction as is also illustrated in WO 03/066705. One of the synthesis conditions is the copolymerization temperature. It was found that copolymers produced at 110° C. show somewhat better initial mechanical properties than copolymers with a similar composition and produced at 120° C.

A polymerization temperature lower than 110° C. will result in a lower conversion and a considerable longer polymerization time to obtain high conversions. Also, homogeneous mixing of the monomers is more difficult at lower temperatures (lactide melts at about 125° C.).

Although a high conversion generally will give a copolymer of a higher purity, the required purity can also be obtained easily by extraction of unreacted monomers using organic solvents.

The composition of the prepared copolymer may be determined using 1H-NMR at 300 MHz of solutions of the copolymer in deuterated chloroform. It is noted that the relative starting amounts of lactide and ε-caprolactone monomers used to synthesize the copolymer may differ significantly from the amount that is actually incorporated into the copolymer, as a result of incomplete conversion. The actual amount of monomers in the copolymers of the present invention (e.g. expressed as lactide content in the polymer, rather than relative amount of starting materials) can always be assessed by 1H-NMR at 300 MHz of solutions of the copolymer in deuterated chloroform.

The intrinsic viscosity may be used as a parameter which reflects the molecular weight, as will be explained in more detail below.

Preferred temperature ranges for the copolymerization reaction are from 100° C.-130° C., more preferably from 110-120° C. A higher polymerization temperature, generally results in a higher conversion but a lower molecular weight and shorter sequences of monomers in the copolymer.

The distribution of monomers in the copolymer may have a large effect on its properties. Since lactide and ε-caprolactone have different reactivities, the copolymer will have a more or less blocky structure. The length of the copolymer units consisting of one type of monomer (average sequence length, $L_{Lac}$ and $L_{Cap}$) is determined by the polymerisation conditions and monomer composition: higher polymerisation temperature, longer polymerization time and higher catalyst concentration result in smaller average sequence lengths (more transesterification takes place). A larger content of one of both monomers in the polymer will result in a larger average sequence length of this monomer.

Also, the L/D ratio of the lactide effects the average sequence lengths and therefore the other polymer properties (see results presented in Table 2).

The average lactide sequence length is generally higher in copolymers with a L/D ratio away from unity, such as L/D=85/15 than in similar copolymers with a L/D ratio equal or close to unity, such as L/D=50/50, when prepared under the same polymerisation conditions. Since the reactivity of L- and D-Lactide is the same, the average sequence length must be determined by the transesterification rate, which is lower in copolymers with L/D=85/15 than in copolymers with L/D=50/50, under the same conditions.

A suitable polymerization time is co-determined by the other polymerization conditions, in particular by the polymerization temperature and amount of catalyst used. Generally, the polymerization time ranges from 3-40 days, preferably from 5-13 days. Also, a longer polymerization time generally results in a higher conversion but a lower molecular weight and smaller sequences of monomers in the polymer. With a catalyst concentration of M/I=9000-12000 the preferred polymerisation time and temperature vary from a minimum of 3 days at 130° C. to a maximum of 40 days at 100° C. With lower catalyst concentration, the polymerisation time must be longer at the same temperature.

As mentioned before, as an example, nerve caps of 65:35 (85/15 L/D)lactide-ε-caprolactone have better mechanical properties than nerve caps with a 50:50 monomer ratio. Both the biodegradable polymer composition and the method of preparation of the copolymer determine the mechanical properties of the nerve cap: a low lactide content (50%) and a very long polymerisation time of 22 days at 130° C. will result in a complete transesterification of the monomers, giving smaller average monomer sequence lengths. In an ideal random 50:50 copolymer the average lactide and caprolacton sequence length, $L_{Lac}$ and $Lc_{Cap}$, will be 4 and 2, respectively (H. R. Kricheldorf and I. Kreiser, J. Macromol. Sci. Chem., A24 (11), 1345, (1987)). The monomer distribution in the prior art copolymer is completely random. Therefore, the small average lactide sequence length will result in poorer mechanical properties (e.g. modulus, tensile strength or toughness) of the 50:50 copolymer compared to those of the copolymers with a larger lactide content (and thus with a longer average lactide sequence length).

Ultimately, after prolonged polymerisation time and/or high polymerisation temperature, the monomer distribution will be completely random in all cases (all L/D ratios). However, of two copolymers with a similar average lactide sequence length, the one with a L/D ratio away from unity (e.g. 85/15) shows better mechanical properties than the one with a L/D ratio equal to unity. This proves that not only the size of the average monomer sequence lengths, but also the L-lactide content of the lactide sequence determines the mechanical properties. These results are confirmed by the data shown in Table 2.

Another important property of the copolymers of the present invention is the molecular weight and in particular the molecular weight distribution. The molecular weight (distribution) may e.g. be determined using gel permeation chromatography (GPC). More conveniently, however, the molecular weight is estimated using a standardized intrinsic viscosity assay (ISO 1628-1). The value for the intrinsic viscosity ([η]) thus obtained (expressed in dL/g) may be converted into the an average molecular weight (Mw) by using the well-known Mark-Houwink expression: $[\eta]=KM\omega^{a}$, wherein K and a are polymer and solvent specific parameters. For lactide-ε-caprolactone copolymers having a lactide content of 45-55% the Mark-Houwink constants were determined experimentally using GPC: K=3.303 10-3 and a=0.548. Similarly, the number-average molecular weight (Mn) may be correlated to the intrinsic viscosity: [η]=1.019 10-3·Mn0.659, wherein the parameters were also determined using GPC. These values can also be applied to the copolymers of this invention with a higher lactide content.

Preferred polymeric materials of the present invention are those having a molecular weight that corresponds to an intrinsic viscosity, as assessed as described above, of more than 4 dL/g, preferably of more than 5 dL/g, more preferably of more than 5.5 dL/g. The molecular weight distribution or polydispersity (Mw/Mn), as determined using GPC) is preferably less than 1.8, more preferably less than 1.5.

The properties of the polymeric material, in particular the molecular weight (distribution), may be controlled by varying the amount of catalyst used in the polymerization reaction. Particularly good results are obtained by employing the catalyst in an amount such that the molar ratio of lactide and ε-caprolactone monomers to the catalyst (M/I) is from 1000-100000, preferably from 9000-12000. Lower M/I ratios (corresponding to a high catalyst concentration) generally result in faster polymerization and higher conversion, resulting in lower molecular weight and shorter sequences of monomers in the polymer. Higher M/I ratios generally give a higher molecular weight and longer sequences of monomers in the polymer. Suitable catalysts for this purpose are known to the skilled person. Particularly suitable are $Sn(oct)_2$ catalysts.

Of course, since the above-mentioned parameters (including polymerization time, polymerization temperature, initial monomer ratio and catalyst concentration) are correlated, optimal values for each of these parameters will differ per case. These optimal values can, however, easily be found in carrying out the invention, optionally by carrying out some routine experiments.

The copolymers of the present invention may be used in a variety of applications, in particular to provide the above-mentioned degradable devices for medical purposes, particularly to provide nerve cap. The polymers of the present invention can e.g. be processed into films, sheets, tubes, rods, plugs, microspheres or meshes, either solid or porous. Pores may vary from small and non-interconnected to large and interconnected. Microporous films (membranes) may also be produced of this material (e.g. having pore sizes as small as 5 µm).

The biodegradable materials of the present invention have excellent properties, which include mechanical strength (tensile strength, modulus, strain at break, suture strength), thermal properties (glass transition temperature, crystallisation) and swelling (water uptake, increase of volume). Important for application as a nerve cap is the retention of its mechanical strength and compressibility.

Another aspect of the present invention is directed at a method to obtain said nerve cap. This method comprises providing a tubular body (herein also referred to as a tube) essentially consisting of biodegradable polymeric material and closing said tube by pressing it between two surfaces such that a tube closed in the radial direction is obtained.

The tube essentially consisting of biodegradable polymeric material means that the tube consists of at least 90%, preferably at least 95%, most preferably at least 99% biodegradable polymeric material.

The tube may be provided by a dip-coating process as is for instance disclosed in WO 03/066705. To this end, the biodegradable polymeric material may be dissolved in a suitable solvent (e.g. chloroform) and dip-coated on mandrels with various dimensions (length and diameter).

In a particular embodiment of the present invention, the tube may first be cut into smaller tubes of appropriate length after which one open end may be closed by pressing the open end between two surfaces. Alternatively, the tube may be pressed at different locations along the longitudinal direction of the tube, thereby closing the tube at these different locations. This step is following by cutting the closed tube just next to these closed locations thereby obtaining a plurality of tubular bodies having one open and one closed end.

The shape of the surfaces should match, viz. when the surfaces are placed on top of each other there should be no significant void remaining between the surfaces such that the open end does not close. Both surfaces may for instance be flat of curved with identical curvatures.

In an alternative embodiment, the provided tube may be cut in smaller tubes with two open end of about twice the desired length of said nerve cap. Subsequently, the resulting smaller tube of this particular embodiment may be closed in the center of the longitudinal direction of the smaller tube by pressing it between two surfaces. The closed tube is subsequently cut into two tubular bodies, each having an open end and a closed end.

In other embodiment of the present invention, the provided tube may be cut and closed in a single step. This may be achieved by selecting appropriated devices for cutting and closing.

By said pressing the biodegradable polymeric material softens and fuses together and upon cooling down the biodegradable polymeric material is bound on a molecular level and the tubular end is irreversible closed. Optionally, some heating may be applied together with the pressing such that the polymeric material sufficiently melts.

Preferably, the applied pressure in the pressing step is between 1 to 25 bar, more preferably between 1 and 10 bar. When heating is applied, this may be done by heating one or both of said flat surfaces. Typically, suitable temperatures of the flat surface are dependent on the Tg of the biodegradable polymeric material. Preferred temperature range from Tg to 180° C., typically from −12 up to 180° C.

A third parameter that may influence the pressing step is the time of pressing. The closer the temperature is to the Tg of the biodegradable polymeric material, the higher the pressure and/or the longer the pressing time. Typical pressure times are 1 second to 4 minutes, preferably between 1 and 120 second.

In another aspect of the present invention, the distal end of the mandrel having a blunt distal end may be used to obtained the a tubular body with a closed end. Since, the biodegradable polymeric material is also deposited during a clip-coating process on said blunt distal end a tube is obtained having one closed end and one open end. This tube may be cut in the appropriated length to obtain the tubular body of said nerve cap. Hence, in this particular embodiment, the closing of an open end as described herein above is not required.

In a preferred embodiment of the present invention, said nerve cap has at least one tab, preferably at the closed end of the tubular body of the cap. This tab may facilitate the immobilization of the nerve cap in the tissue by suture. Preferably, said tab is obtained simultaneously when the closed end is obtained by pressing the tube between the two said surfaces.

FIG. 3 is an illustration of a preferred embodiment wherein tube (1) is provided followed by simultaneously obtaining the closed end and the tab (4) by pressing the tube between the two surfaces (5).

It was surprisingly found that when the nerve cap comprises the poly(DL-lactide-co-ε-caprolactone) copolymer in accordance with the present invention, this greatly facilitates the way the closed end of the tube and said tab can be obtained. It was found that no adhesives are required for obtaining the closed end and the tab from an open-ended tube, but that this can be obtained by pressing the tube between two surfaces under a mildly elevated temperature and pressure.

For instance, good results are obtained by pressing the tube between the two surfaces at 2 to 15 bar, preferably 3 to 10 bar, more preferably 6 to 7 bar and/or at a temperature of 50 to 200° C., preferably 70 to 150° C. The tube is preferably pressed between the two surfaces at these pressures and/or temperatures for 2 to 30 seconds, preferably 5 to 20 second, more preferably 7 to 15 seconds, most preferably about 10 seconds. For these conditions, a static sealer bar as commercially available from Audion Elektro B.V. (Weeps, the Netherlands) may for instance be used.

The quality of the closing of the tube by pressing it between two surfaces (the seal) can be determined visually and analytically. Visual inspection may for instance reveal peeling, rupture or other inconsistencies of the closed end. Preferably, the closed end shows an homogenous closure upon visual inspection.

Analytical methods include a tensile test, which may be carried out for instance using an Instron™ tensile tester. Tensile characteristics of the closed end and tab that may be determined are the modulus (MPa) and toughness (J) and stress at present point (tensile strain 0.1 mm/mm) (MPa).

The modulus of the closed end and the tab is typically between 5 to 50 MPa, preferably between 10 to 30 MPa, the toughness is typically between 0.5 and 2 J and/or the stress at present point is generally between 0.5 and 2 MPa.

One of the important aspects of devices of the present invention with respect to their tensile strength is that the devices may be prepared such that they will break, tear and/or rupture in the bulk material, while preferably the seal of the capping stays intact, or substantially intact. If the seal starts to peel and the rest of the bulk material is still intact then the nerve capping device is generally considered not to be suitable for application as a nerve cap.

In a further preferred embodiment, the tab comprises one or more holes to facilitate the immobilization of the nerve cap in the tissue. In this particular embodiment, the tab does not need to be punctured by a needle such that the risk of rapture of the tab upon immobilization is reduced.

Figure 1:
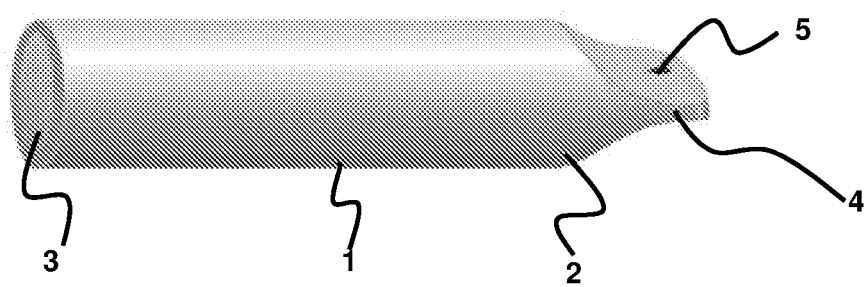
FIG. 1 is a schematic three-dimensional representation of an embodiment in accordance with the present invention. The tubular body (1) with a closed end (2) and an open end (3) are shown, as well as tab (4) with hole (5).
Figure 2:
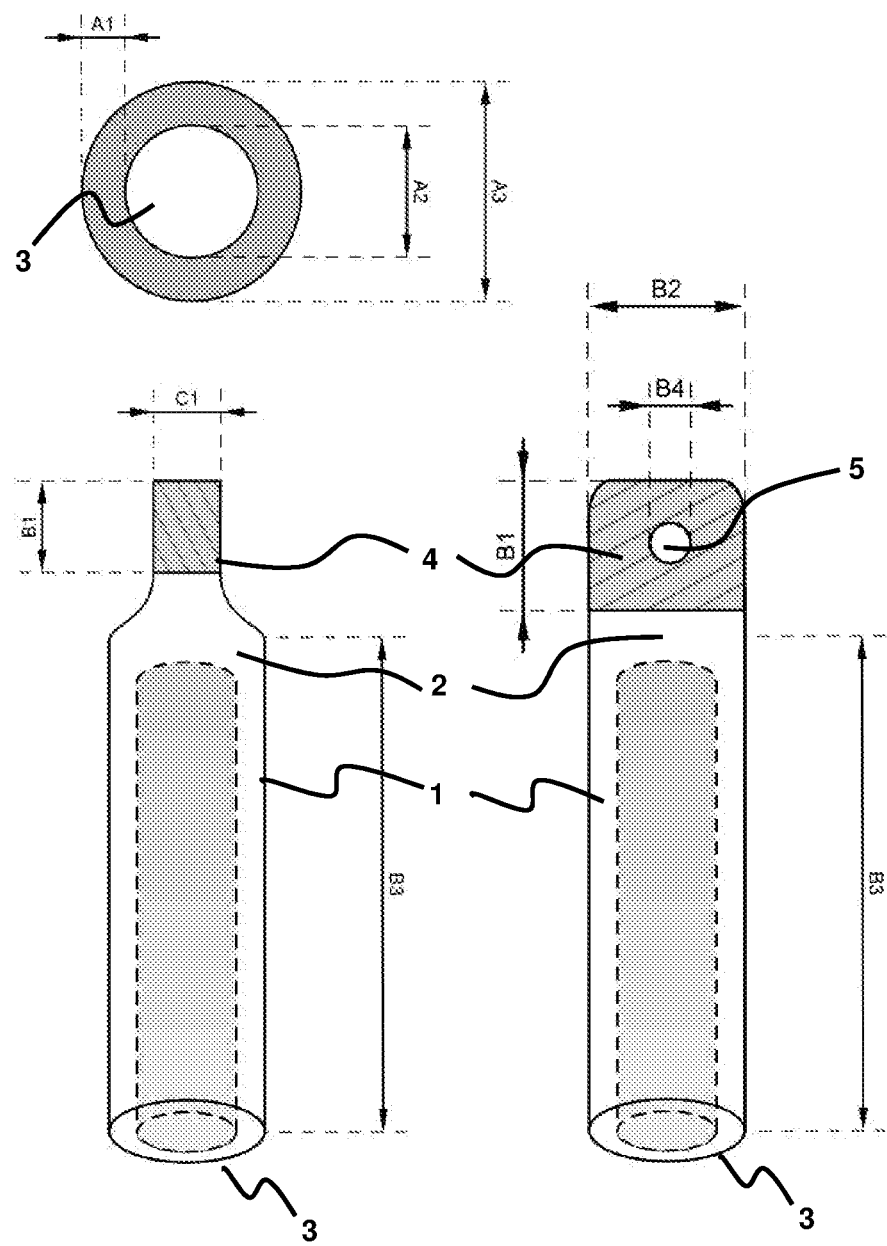
FIG. 2 is a schematic two-dimensional representation with different points of view (top and frontal) of the same embodiment in accordance with the present invention.
Figure 3:
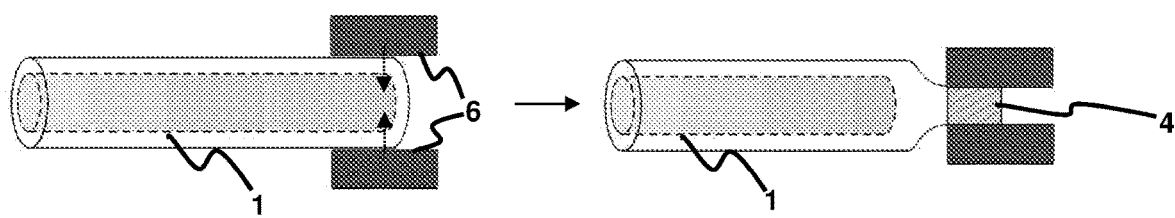

Some of the dimensions, of the nerve cap, such as the length and inner diameter (A2) of the nerve cap, may depend on the location of the nerve stump that is to be capped by the nerve cap. For instance, nerves in the thigh are typically thicker than nerves in the arm. Preferably, the tubular body has a inner diameter (A2) of 1.35 mm to 10.40 mm and a length (B3) of 10 mm to 40 mm.

Some of the dimensions, such as e.g. wall thickness (A1) may be used to modify the mechanical properties and/or biodegradation rate of the nerve cap. The wall thickness (A1) of the tubular body (1) is preferably between 0.2 mm and 1.5 mm, more preferably between 0.4 mm and 0.75 mm.

The dimension of the tab is generally in the range of 3-14 mm (B2) by 3-5 mm (B1). The thickness (C1) of the tab is typically about 1.8 to 2 times the thickness (A1) of the wall of the tube.

A further aspect of the present invention is a method to treat and/or prevent symptoms caused by neuroma by capping the nerve stump with an nerve cap in accordance with the present invention. In certain embodiment, in particular when a neuroma has already developed prior to treatment, the neuroma is first removed before the nerve stump is capped.

The capping of the nerve stump in accordance with the present invention may prevent or treat the symptoms caused by neuroma's. This means that the growth of neuroma may be hampered or the symptoms caused by neuroma will be limited. Hence, the nerve cap in accordance with the present invention may also be used before the development of (symptomatic) neuroma, e.g. just after amputation or cutting of the nerve.

For the purpose of clarity and a concise description features are described herein as part of the same or separate embodiments, however, it will be appreciated that the scope of the invention may include embodiments having combinations of all or some of the features described.

The invention claimed is:

1. A nerve cap for covering a nerve stump, comprising a tubular body with a closed end and an open end and comprising biodegradable polymeric material, which cap has at least one tab comprising one or more holes, wherein said at least one tab is located at the closed end of the tubular body of the nerve cap, wherein the biodegradable polymeric material comprises a poly(DL-lactide-co-ε-caprolactone) copolymer having a lactide content of 51-75 mol %.

2. The nerve cap according to claim 1, wherein the at least one tab has a modulus of between 5 to 50 MPa, a toughness of between 0.5 and 2 J and/or a stress at present point of between 0.5 and 2 MPa.

3. The nerve cap according to claim 1, wherein the fraction of the D-enantiomer or L-enantiomer of the lactide is from 65 mol % to 95 mol %.

4. The nerve cap according to claim 1, wherein the copolymer has a lactide content of 55-70 mol %.

5. The nerve cap according to claim 4, wherein the fraction of the D-enantiomer or L-enantiomer of the lactide in the polymeric material is from 65 mol % to 95 mol %.

6. The nerve cap according to claim 1, wherein the polymeric material has a polydispersity (Mw/Mn) of less than 1.8.

7. The nerve cap according to claim 1, wherein the polymeric material has an intrinsic viscosity of more than 4 dL/g.

8. The nerve cap according to claim 1, wherein the at least one tab has a modulus of between 10 to 30 MPa.

9. The nerve cap according to claim 1, wherein the fraction of the D-enantiomer or L-enantiomer of the lactide is from 70 mol % to 90 mol %.

10. The nerve cap according to claim 1, wherein the polymeric material has a polydispersity (Mw/Mn) of less than 1.5.

11. The nerve cap according to claim 1, wherein the polymeric material has an intrinsic viscosity of more than 5 dL/g.

12. The nerve cap according to claim 1, wherein the nerve cap is configured to be immobilized in tissue by suture.

13. A method of treating and/or preventing symptoms caused by neuroma comprising capping said neuroma with the nerve cap according to claim 1.

* * * * *